United States Patent
Matula

[19]

[11] Patent Number: 6,007,495
[45] Date of Patent: Dec. 28, 1999

[54] BIOPSY APPARATUS AND METHOD

[75] Inventor: Paul A. Matula, Brookfield, Conn.

[73] Assignee: United States Surgical Corporation, Norwalk, Conn.

[21] Appl. No.: 09/012,106

[22] Filed: Jan. 22, 1998

[51] Int. Cl.$^6$ .............................................. A61B 10/00
[52] U.S. Cl. ........................................................ 600/564
[58] Field of Search ................................. 600/564–567; 606/167, 170

[56] References Cited

U.S. PATENT DOCUMENTS

| | | |
|---|---|---|
| 3,989,033 | 11/1976 | Halpern et al. . |
| 4,461,305 | 7/1984 | Cibley ..................................... 600/564 |
| 4,682,606 | 7/1987 | DeCaprio . |
| 4,735,215 | 4/1988 | Goto et al. . |
| 4,776,346 | 10/1988 | Beraha et al. . |
| 4,881,550 | 11/1989 | Kothe ...................................... 600/564 |
| 4,926,877 | 5/1990 | Bookwalter . |
| 5,018,530 | 5/1991 | Rank et al. . |
| 5,152,780 | 10/1992 | Honkanen et al. ..................... 600/564 |
| 5,183,052 | 2/1993 | Terwilliger . |
| 5,192,291 | 3/1993 | Pannek, Jr. . |
| 5,195,533 | 3/1993 | Chin et al. . |
| 5,195,540 | 3/1993 | Shiber . |
| 5,197,482 | 3/1993 | Rank et al. . |
| 5,201,759 | 4/1993 | Ferzli ...................................... 600/564 |
| 5,221,269 | 6/1993 | Miller et al. . |
| 5,224,488 | 7/1993 | Neuffer . |
| 5,224,945 | 7/1993 | Pannek, Jr. . |
| 5,226,909 | 7/1993 | Evans et al. . |
| 5,226,910 | 7/1993 | Kajiyama et al. . |
| 5,234,426 | 8/1993 | Rank et al. . |
| 5,246,011 | 9/1993 | Caillouette . |
| 5,372,588 | 12/1994 | Farley et al. . |
| 5,443,475 | 8/1995 | Auerbach et al. ...................... 600/564 |
| 5,488,958 | 2/1996 | Topel et al. . |
| 5,499,989 | 3/1996 | Le Bash ................................. 600/567 |

Primary Examiner—Max Hindenburg

[57] ABSTRACT

A biopsy apparatus for obtaining tissue samples includes a housing, an elongated member slidably and rotatably mounted in the housing and a blade having a stem portion pivotally mounted on the elongated member and moving transversely relative to a longitudinal axis of the elongated member between a stowed position and a deployed position. A method of sampling tissue includes the steps of providing the biopsy apparatus, inserting the elongated member into a tissue mass, deploying the blade, severing a tissue sample from the tissue mass by proximally retracting and rotating the elongated member, removing the elongated member from the tissue mass and extracting the tissue sample from a patient.

32 Claims, 10 Drawing Sheets

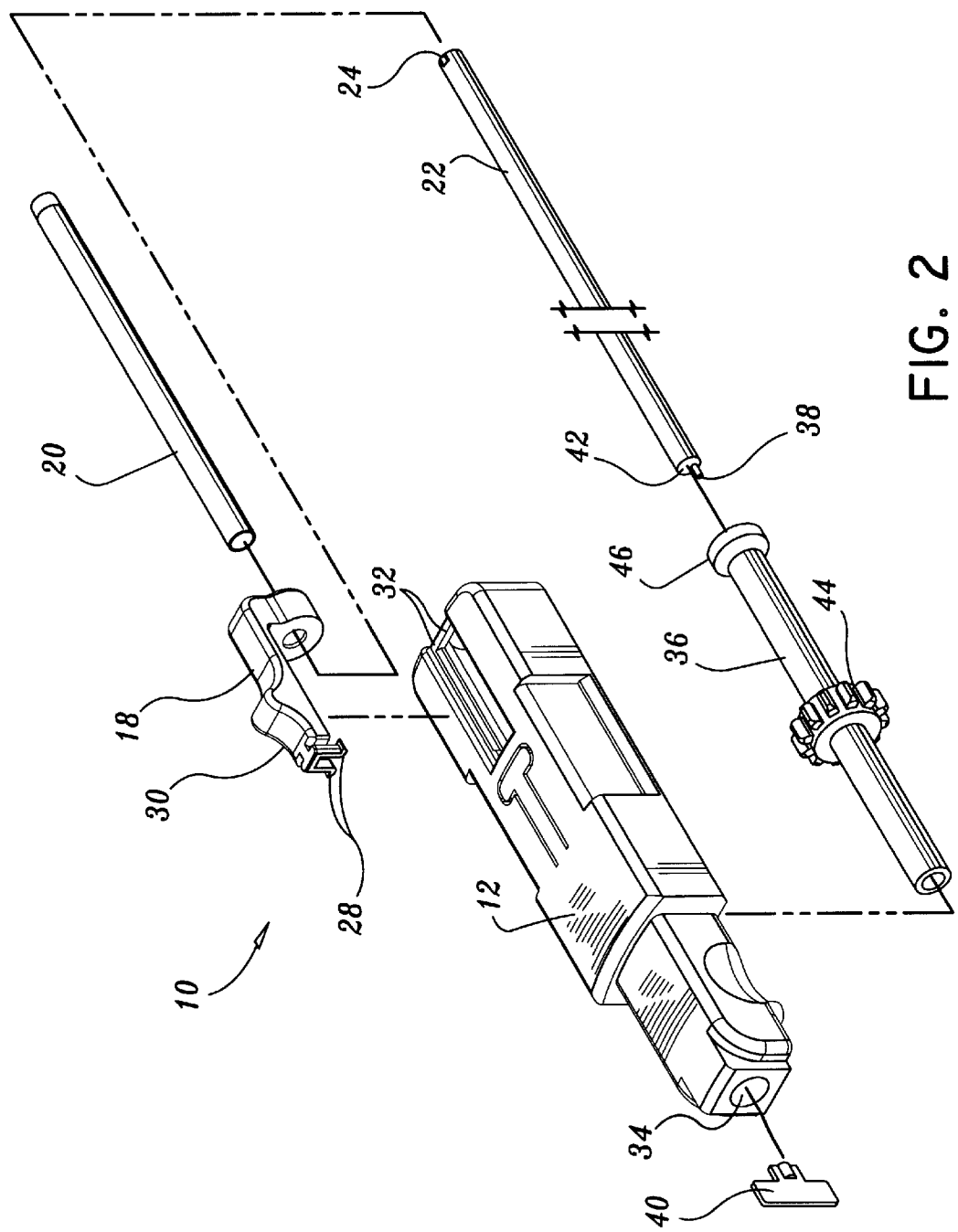

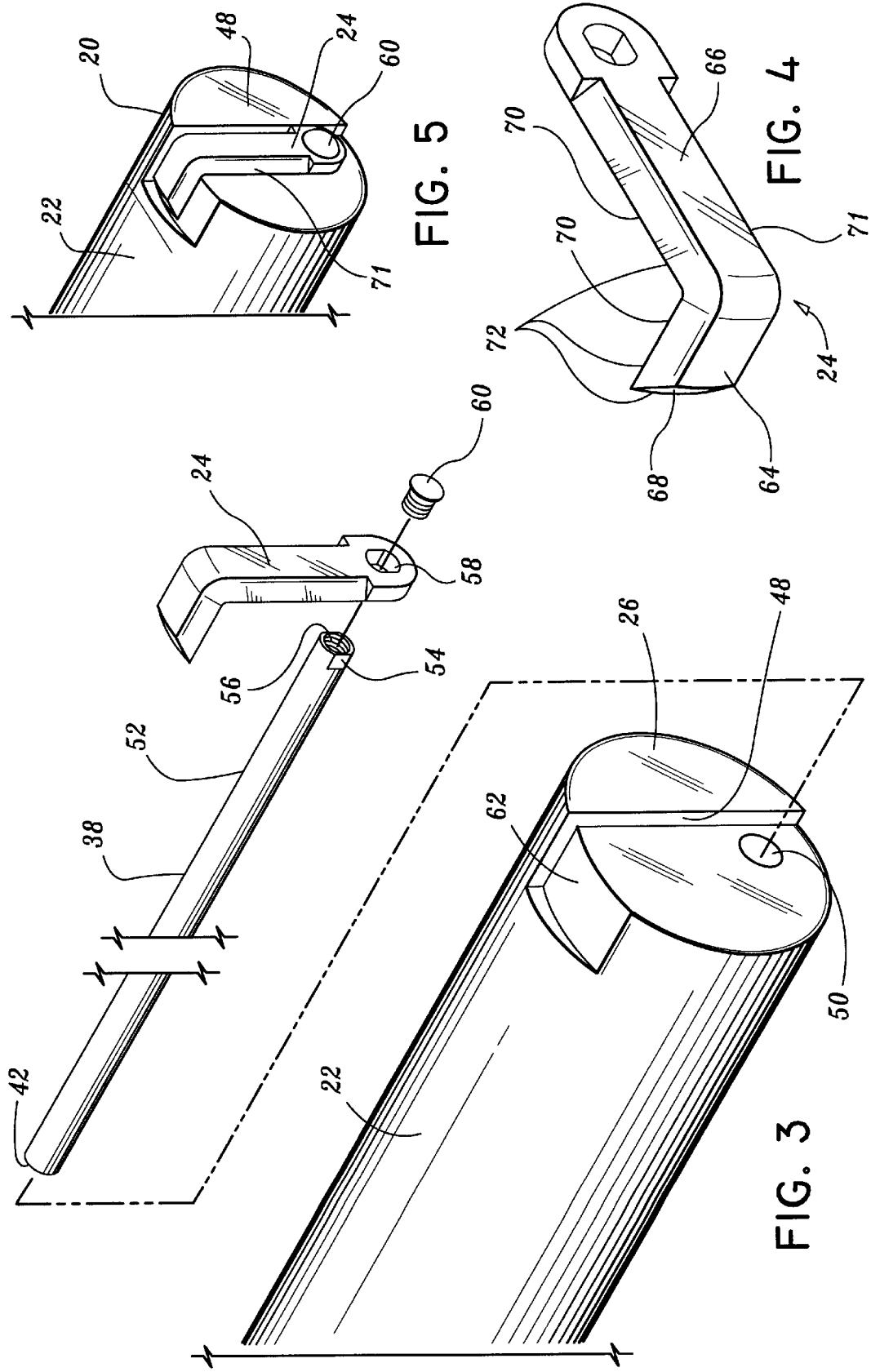

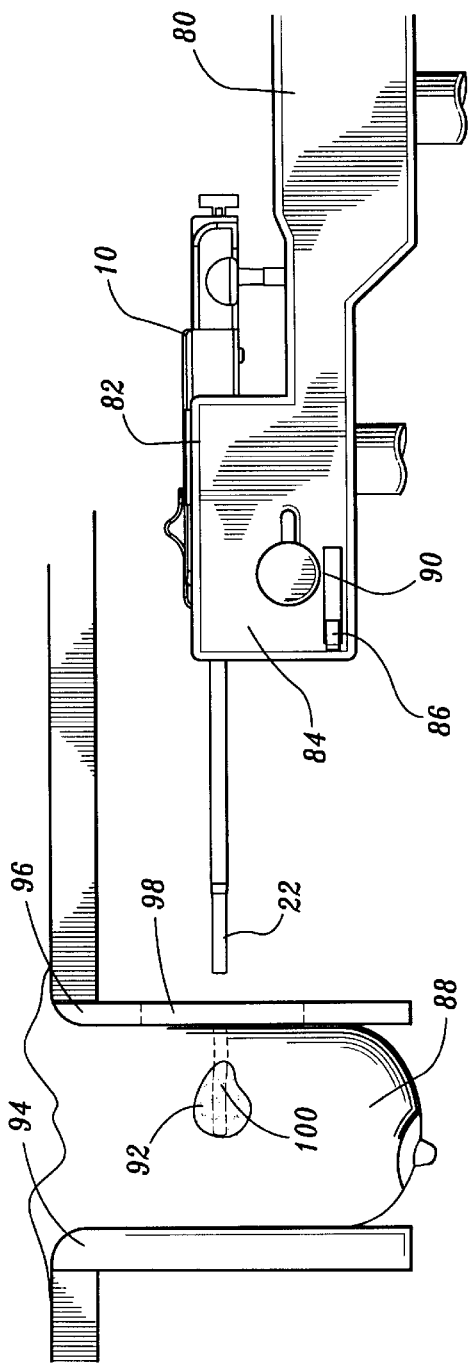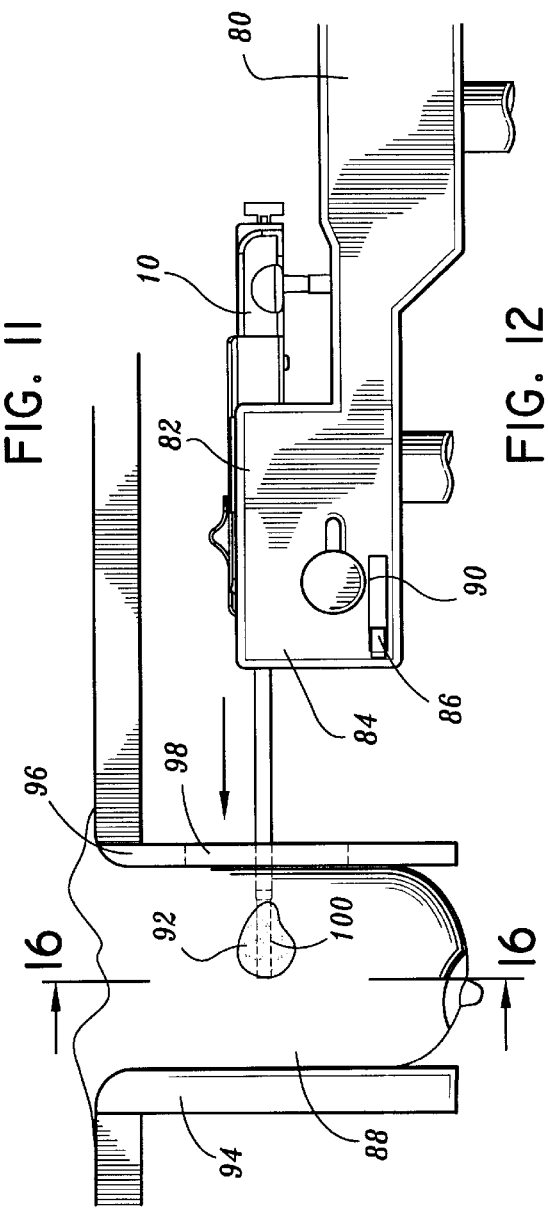

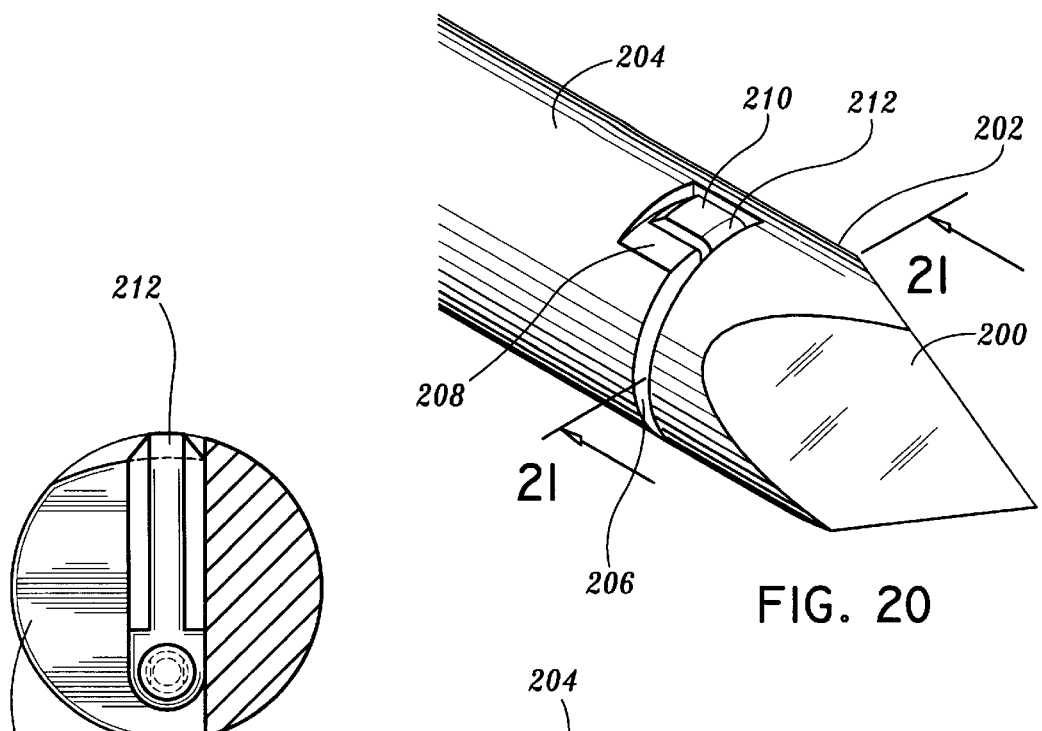
FIG. 20
FIG. 21
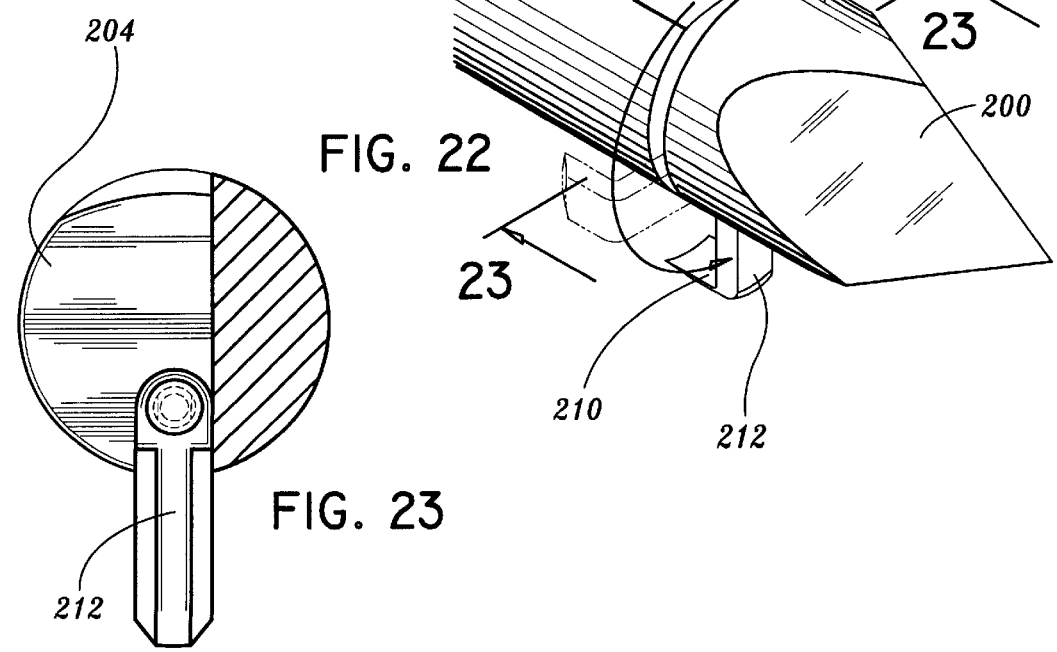
FIG. 22
FIG. 23

6,007,495

BIOPSY APPARATUS AND METHOD

BACKGROUND

1. Technical Field

This disclosure relates to an apparatus and method for the biopsy of tissue specimens and, more particularly to a percutaneous biopsy cutting blade and method.

2. Background of Related Art

It is often necessary to sample tissue in order to diagnose and treat patients with cancerous tumors, pre-malignant conditions and other diseases or disorders. Typically, in the case of suspected cancerous tissue, when the physician establishes by means of procedures such as palpation, x-ray or ultrasound imaging that suspicious conditions exist, a biopsy is performed to determine whether the cells are cancerous. Biopsy may be done by an open or percutaneous technique. Open biopsy removes the entire mass (excisional biopsy) or a part of the mass (incisional biopsy). Percutaneous biopsy on the other hand is usually done with a needle-like instrument and may be either a fine needle aspiration (FNA) or a core biopsy. In FNA biopsy, individual cells or clusters of cells are obtained for cytologic examination and may be prepared such as in a Papanicolaou smear. In core biopsy, as the term suggests, a core or fragment of tissue is obtained for histologic examination which may be done via frozen section or paraffin section.

The type of biopsy utilized depends in large part on the circumstances present with respect to the patient and no single procedure is ideal for all cases. Core biopsy, however, is extremely useful in a number of conditions and is being used more frequently.

Intact tissue from the organ or lesion is required by medical personnel in order to arrive at a definitive diagnosis regarding the patient's condition. The tissue extracted must be indicative of the organ or lesion as a whole. In the past, to obtain tissue from organs or lesions within the body, surgery had to be performed in order to locate, identify and remove the tissue. With present technology, medical imaging equipment such as x-rays, fluoroscopy, computer tomography, ultrasound, nuclear medicine and magnetic resonance imaging, may be used. These technologies make it possible to identify small abnormalities even deep within the body. However, definitive tissue characterization still requires obtaining adequate tissue samples to characterize the histology of the organ or lesion.

In the example of breast cancers, mammography can identify non-palpable (not perceptible by touch) breast abnormalities earlier than they can be diagnosed by physical examination. Most non-palpable breast abnormalities are benign but some are malignant. When breast cancer is diagnosed before it becomes palpable, breast cancer mortality can be reduced. It is still difficult to determine if pre-palpable breast abnormalities are malignant, as some benign lesions have mammographic features which mimic malignant lesions and some malignant lesions have mammographic features which mimic benign lesions. Thus, mammography has its limitations. To reach a definitive diagnosis, tissue from within the breast must be removed and examined under a microscope.

With the introduction of stereotactic and ultrasound guided percutaneous breast biopsies, an alternative to open surgical breast biopsy became an option. These guidance systems have become more accurate and easier to use than when they were first introduced. Biopsy guns were introduced for use in conjunction with these guidance systems. The biopsy guns were limited because placement of the gun had to be done very accurately because only one small core could be obtained per insertion at any one location. To sample the lesion thoroughly, many separate insertions of the instrument had to be made.

Many biopsy procedures would benefit from larger tissue samples being taken, for example, tissue samples as large as 10 mm across. Many of the previously developed devices required multiple punctures into the breast or organ in order to obtain the necessary samples. This practice is both tedious and time consuming.

One further solution to obtain a larger tissue sample is to utilize a device capable of taking multiple tissue samples with a single insertion of an instrument. An example of such a device is found in U.S. Pat. No. 5,195,533 to Chin et al. which describes a technique for extracting multiple samples with a single insertion of the biopsy device. Generally, such biopsy instruments extract a sample of tissue from a tissue mass by either drawing a tissue sample into a hollow needle via an external vacuum source or by severing and containing a tissue sample within a notch formed on a stylet. Typical of such devices utilizing an external vacuum source are U.S. Pat. No. 5,246,011 issued to Cailouette and U.S. Pat. No. 5,183,052 issued to Terwiliger. These designs are usually limited in the size of the sample extracted to the outside diameter of the needle or tube in which the tissue sample is to be carried.

It would be advantageous to provide only a small opening in the skin of the breast, but be able to obtain large biopsy samples. Therefore, a need exists for a percutaneous biopsy apparatus and method which can extract a biopsy sample larger than the skin opening in the patient through which it must be drawn.

SUMMARY

A biopsy apparatus for obtaining tissue samples includes a housing, an elongated member slidably and rotatably mounted in the housing and a blade. The blade has a stem portion pivotally mounted on the elongated member. The blade is movable transversely to a longitudinal axis of the elongated member and configurable between a stowed position and a deployed position. The blade may have an angled leg portion transversely orientated relative to the stem portion and be substantially parallel to the longitudinal axis of the elongated member. An actuator may be included which is operatively associated with the blade to move the blade between the stowed and deployed positions.

A shaft rotatably disposed within the elongated member may be used to rotate the blade. The shaft may be turned by a key attached at a proximal end of the shaft. The key may be selectively movable from a first position corresponding to the stowed position of the blade and a second position corresponding to the deployed position of the blade. The elongated member may have stops formed thereon to secure the key in the first position corresponding to the stowed position of the blade and the second position corresponding to the deployed position of the blade.

A distal end of the elongated member may further include a step thereon for preventing rotation of the blade during operation in the deployed position. The elongated member may be positioned by a guidance system. A penetrating tip may be mounted at a distal end of the elongated member. The elongated member may also define a recess for stowing the angled leg portion of the blade when in its stowed position. The blade may be dimensioned and configured to be positioned a first distance away from a central longitudinal axis of the elongated member in the stowed position and a second distance away from the central longitudinal axis of the elongated member in the deployed position. A gear shaft with a gear mounted thereon may be included. The gear shaft attaches to the elongated member and may be positioned on the housing such that translation and rotation of the elongated member are controlled by translating and rotating the gear.

A method of sampling tissue includes the steps of providing a housing, an elongated member slidably and rotatably mounted in the housing and a blade having a stem portion pivotally mounted on the elongated member, and the blade being movable transversely to a longitudinal axis of the elongated member and configurable between a stowed position and a deployed position, inserting the elongated member into a tissue mass, deploying the blade, severing a tissue sample from the tissue mass by proximally retracting and rotating the elongated member removing the elongated member from the tissue mass and extracting the tissue sample from a patient. The step of inserting the elongated member may include clamping a breast, incising the breast at a predetermined location and distally advancing the elongated member being guided by a guidance system through the incision and into the tissue mass.

The step of deploying may include rotating a shaft disposed within the elongated member and attached to the blade at a distal end of the shaft to rotate the blade from a stowed position to a deployed position, and securing the blade in the deployed position. The step of severing may further include the blade having an angled leg portion transversely orientated relative to the stem portion and substantially parallel to the longitudinal axis of the elongated member and rotating the elongated member and proximally retracting the elongated member at a rate of the longitudinal distance of one angled leg portion of the blade per rotation to create a spiral cut to sever a tissue sample from the tissue mass.

BRIEF DESCRIPTION OF THE DRAWINGS

Various embodiments are described herein with reference to the drawings, wherein:

FIG. 2 is a perspective view of the biopsy apparatus of FIG. 1 with parts separated;

FIG. 3 is an enlarged partial perspective view of a distal end of a rod with parts separated showing a blade and a shaft of the biopsy apparatus of FIG. 1;

FIG. 4 is a perspective view of the blade;

FIG. 5 is a partial perspective view of the distal end of the biopsy apparatus which shows the blade in a stowed position;

FIG. 11 is a partial side view of a biopsy apparatus showing a clamped breast after insertion of a needle or trocar and prior to the insertion of a rod;

FIG. 12 is a partial side view of a biopsy apparatus showing a clamped breast with a rod inserted into a target tissue mass;

FIG. 20 is a perspective view of another embodiment of a rod showing a penetration tip mounted at a distal end portion of the rod and a blade in a stowed position;

FIG. 21 is a cross-sectional view taken at section line 21—21 as shown in FIG. 20;

FIG. 22 is a perspective view of the embodiment shown in FIG. 20 with a blade in a deployed position; and FIG. 23 is a cross-sectional view taken at section line 23—23 as shown in FIG. 22.

DETAILED DESCRIPTION OF PREFERRED EMBODIMENTS

The present disclosure describes an apparatus and method for the biopsy of tissue specimens and, more particularly, a percutaneous biopsy cutting blade and method. A blade is mounted on a distal end of a rod and is guided into a target tissue mass. Upon reaching the appropriate location, the blade is deployed. The blade is rotated and withdrawn proximally to create a spiral cut and sever a tissue sample from the tissue mass larger than the opening made through the skin of the patient.

Figure 1:
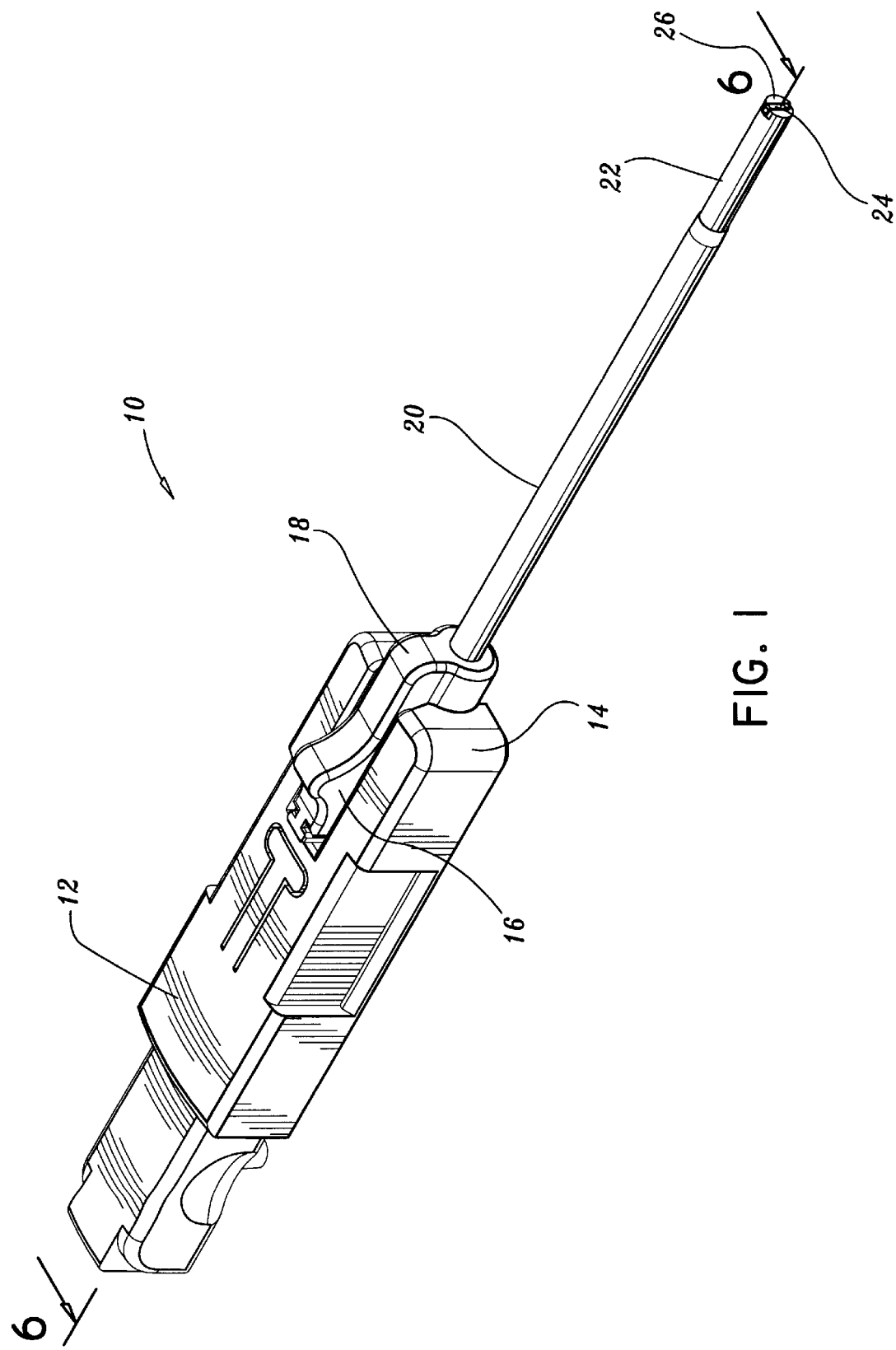
FIG. 1 is a perspective view of one embodiment of a biopsy apparatus constructed in accordance with the preset disclosure.

Referring now in specific detail to the drawings in which like reference numerals identify similar or identical elements throughout the several views, and initially to FIG. 1, one embodiment of a biopsy apparatus is shown generally as apparatus 10. Apparatus 10 includes a housing 12 having a distal end portion 14. Distal end portion 14 defines a channel 16 therein for slidably mounting a slide 18. Slide 18 attaches to a support tube 20. Slide 18 and support tube are dismountable and act as a cannula during surgery to maintain an opening in the skin of a patient. Disposed within support tube 20 is a rod 22. Rod 22 can translate and rotate relative to support tube 20. A blade 24 is mounted on a distal end 26 of rod 22. Details of blade 24 are described further herein.

Referring to FIG. 2, slide 18 has a pair of tabs 28 formed on a proximal end portion 30. Tabs 28 are configured and dimensioned to snap into rails 32 formed on opposite side of channel 16. Tabs 28 and rails 32 engage to slide 18 and support tube 20 while allowing slide 18 and support tube 20 to translate within channel 16. Tabs 28 further allow slide 18 to detach from housing 12.

Housing 12 defines a longitudinal bore 34 formed therethrough. Rod 22 extends through support tube 20, slide 18 and into a gear shaft 36 when assembled. Rod 22 also extends through bore 34. Rod 22 can be made from stainless steel or equivalent materials which are sterilizable and possess the appropriate strength. A shaft 38 is disposed within rod 22 and attaches to blade 24 at a distal end portion 52 (FIG. 3). Shaft 38 is preferably made from a material that is sterilizable with an appropriate torsional rigidity characteristics. Shaft 38 attaches to a blade deployment key 40 at a proximal end 42. During operation, gear shaft 36 which has a gear 44 mounted thereon is translated and rotated to control the translational and rotational motion of rod 22 which is attached to a flanged end 46 of gear shaft 36. Gear 44 may be driven manually or automatically by a driving mechanism (not shown) to translate and rotate gear shaft 36.

Referring to FIG. 3, the distal end 26 of rod 22 is shown. Distal end 26 has a step 48 formed thereon. Step 48 acts as a stop to limit the rotation of blade 24 upon assembly. Rod 22 defines a longitudinal bore 50 formed therethrough to support shaft 38 and allow shaft 38 to rotate therein. Distal end portion 52 forms a set of flats 54 oppositely disposed thereon, and a threaded hole 56 formed therein. Blade 24 defies a hole 58 formed therethrough which has flat sides corresponding to flats 54 formed on distal end portion 52 of shaft 38. Upon assembly blade 24 cannot rotate relative to shaft 38. Blade 24 is attached to shaft 38 by a threaded bolt 60 which engages threaded hole 56 to mount blade 24 on shaft 38. Distal end 26 of rod 22 further defines a recess 62 to provide a location to stow blade 24 during insertion into a patient.

Referring to FIG. 4, blade 24 is generally L-shaped having an angled leg portion 64 and a stem portion 66. Blade 24 can be made from stainless steel or equivalent materials which are sterilizable and possess the appropriate strength. A front edge 68 of angled leg portion 64 and a side edge 70 of both angled leg portion 64 and stem portion 66 are tapered to form a cutting edge 72 thereon for cutting tissue. In addition, a side cutting edge 71 is provided on blade 24 to permit blade 24 to pass through tissue so that blade 24 may be rotated from its stowed position during operation.

Referring to FIG. 5, blade 24 is shown in a stowed position mounted at distal end 26 of rod 22. Angled leg portion 64 is configured and dimensioned to fit within recess 62, while step 48 extends past or at least to the furthest point of blade 24 to shelter blade during insertion into a patient. Cutting edge 72 faces into step 48 to protect cutting edge 72 while side cutting edge 71 faces outward to slice through tissue and enable deployment of blade 24 during operation.

Figure 6:
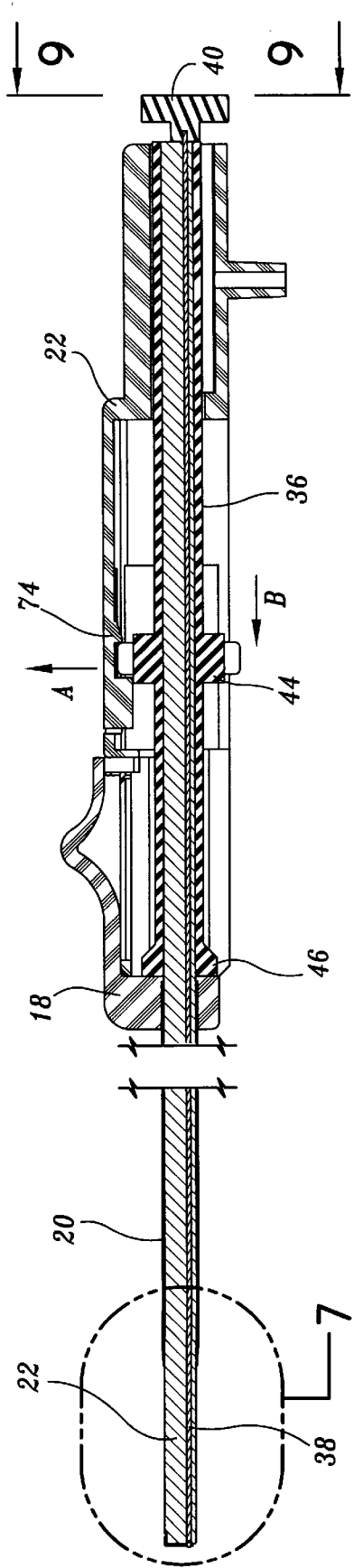
FIG. 6 is a cross-sectional view of the biopsy apparatus taken at section line 6—6 as shown in FIG. 1.

Referring to FIG. 6, a cross section of apparatus 10 is shown. Housing 22 has a camming surface 74 formed thereon. During insertion of apparatus 10 into a patient, rod 22 is located in a distalmost position. Gear shaft 36 and gear 44 are used to translate rod 22 into its distalmost position. Upon insertion, gear 44 engages camming surface 74 deflecting camming surface outwardly in the direction of arrow "A". Gear 44 moves in the direction of arrow "B" passed camming surface 74 and is locked in place when camming surface recoils thereby securing rod 22 in the distalmost position.

Referring to FIGS. 7–10, prior to insertion into the patient, blade 24 is in its stowed position. Key 40 has wings 78 which are captured between stops 76 in both a deployed and stowed positions of blade 24. Key 40 is attached to proximal end 42 of shaft 38. The stowed and deployed positions of blade 24 correspond to wings 78 of key 40 being located between stops 76 formed on rod 22. Stops 76 secure key 40, shaft 38 and blade 24. Rotation of key 40 one half turn rotates blade 24 from the stowed position to the deployed position. Wings 78 are cammed over stops 76 to capture wings 78 therebetween.

Referring to FIGS. 11 and 12, housing 12 is mounted on a driver end guidance platform 80 in order to perform the biopsy procedure. Platform 80 is configured and dimensioned for attachment to an instrument positioning stage of an imaging apparatus. One example of an imaging apparatus is a stereotactic imaging apparatus. One such apparatus is available from LORAD Corporation of Danbury, Conn. or from Fischer Imaging Corporation of Denver, Colo. Alternatively, apparatus 10 may be adapted to fit on any other suitable imaging apparatus such as, for example, ultrasound. Platform 80 is used to stabilize apparatus 10 and provide power and support thereto during the biopsy procedure. Platform 80 includes a partially enclosed area 82 at a distal end portion 84. Partially enclosed area 82 provides structure for maintaining housing base 12 in a secured position relative to platform 80. Platform 80 may also include a motor (not shown) which drives a gear (not shown) that engages gear 44 for rotation and translation of rod 22, and further includes a compression spring (not shown) released by a trigger 86 which serves to shoot apparatus 10 the final distance, approximately ¾ of an inch, into a breast 88. One or more control knobs such as control knob 90 may be provided to control the advancement and retraction of rod 22.

A patient's breast 88 is disposed between a movable clamp 94 and a stationary clamp 96. Movable clamp 94 is moved toward stationary clamp 96 capturing breast 88 therebetween. Upon securing breast 88 in position, an imaging and guidance system (not shown) locates a target tissue mass 92 within breast 88. An nick is made in an appropriate location on breast 88 and a needle or trocar is introduced and guided as it penetrates breast 88. The needle or trocar creates a hole 100 into which rod 22 may be introduced into the breast.

Apparatus 10 is aimed at target tissue mass 92 such that rod 22 is aligned with the direction of advancement of platform 80. Stationary clamp 96 defines an opening 98 therethrough to allow entry into breast 88. Before insertion into breast 88, gear shaft 36 and therefore rod 22 are fully advanced distally. Rod 22 is approximated adjacent the location of the nick into breast 88. Preferably, this is accomplished by the positioning capability of the imaging and guidance system. Rod 22 is advanced distally into breast 88 by release of the stored energy of the compression spring in platform 80, e.g., by activating a trigger release mechanism, so that rod 22 is located within target tissue mass 92, as required. Rod 22 is advanced into target tissue mass 92. The guidance system (not shown) can be used to monitor the location of rod 22 to confirm that it is within target tissue mass 92.

Figure 13:
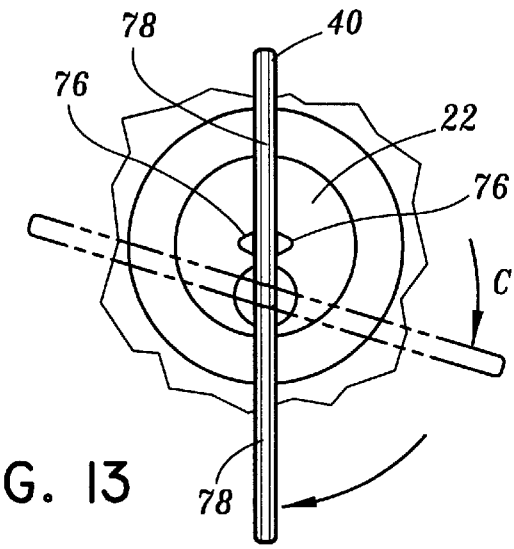
FIG. 13 is a side view of a blade deployment key showing the operational movement of the key.
Figure 14:
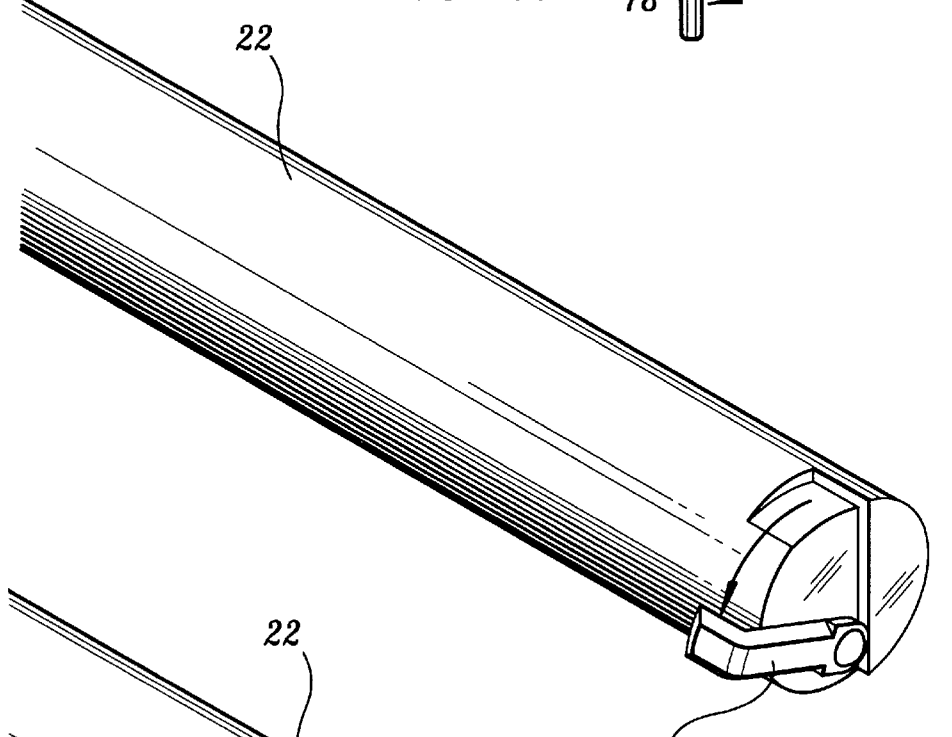
FIG. 14 is a perspective view of a distal end portion of the rod showing the blade being deployed.
Figure 15:
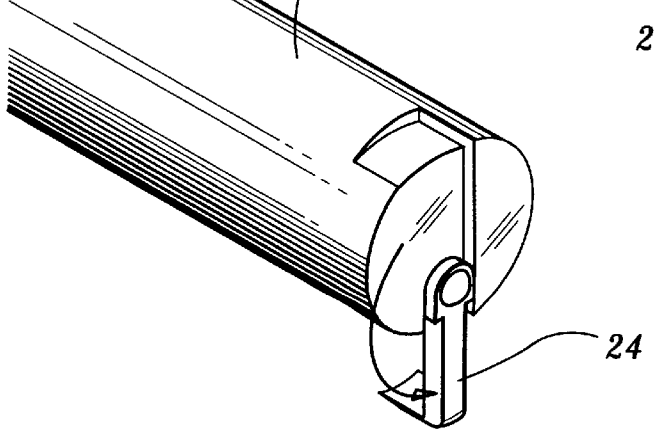
FIG. 15 is a perspective view of a distal end portion of the rod showing the blade in a deployed position.

Referring to FIGS. 13–15, after insertion of rod 22 into breast 88, blade 24 is moved from the stowed position to the deployed position by rotating key 40 in the direction of arrow "C". Wing 78 is removed from between stops 76, key 40 is turned about 180 degrees and resecured between stops 76. This rotation causes the rotation of blade 24 as shown in FIGS. 14 and 15. FIG. 15 shows blade in the deployed position.

Figure 16:
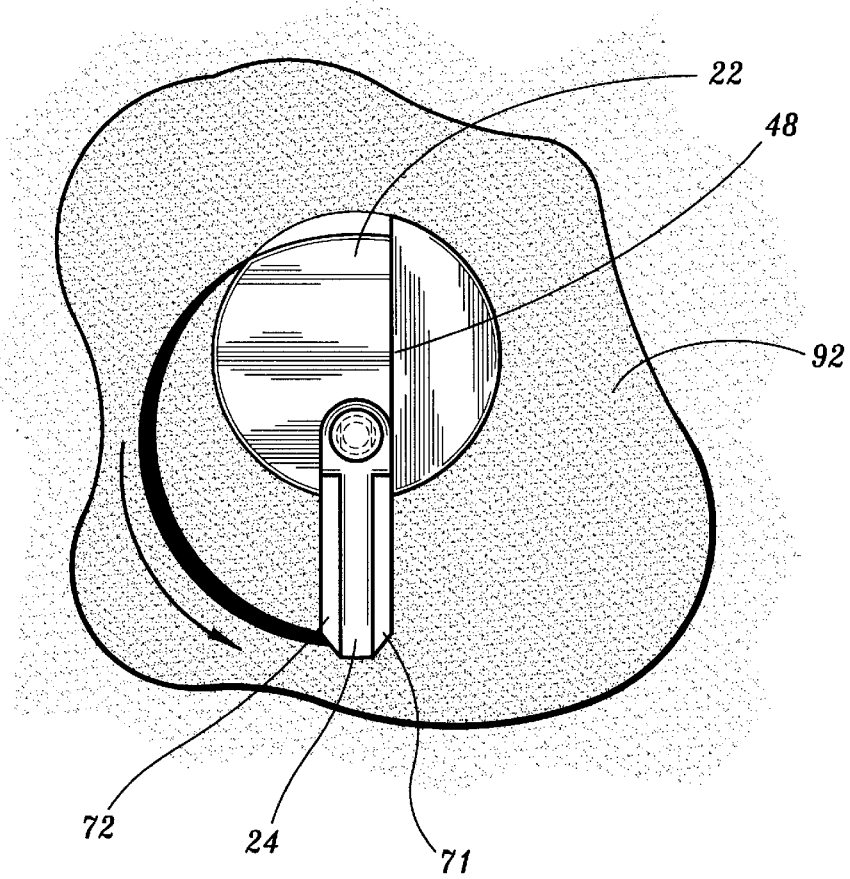
FIG. 16 is a cross-sectional view taken at section line 16—16 of FIG. 12, which shows a distal end portion of the rod having a blade in the deployed position.
Figure 17:
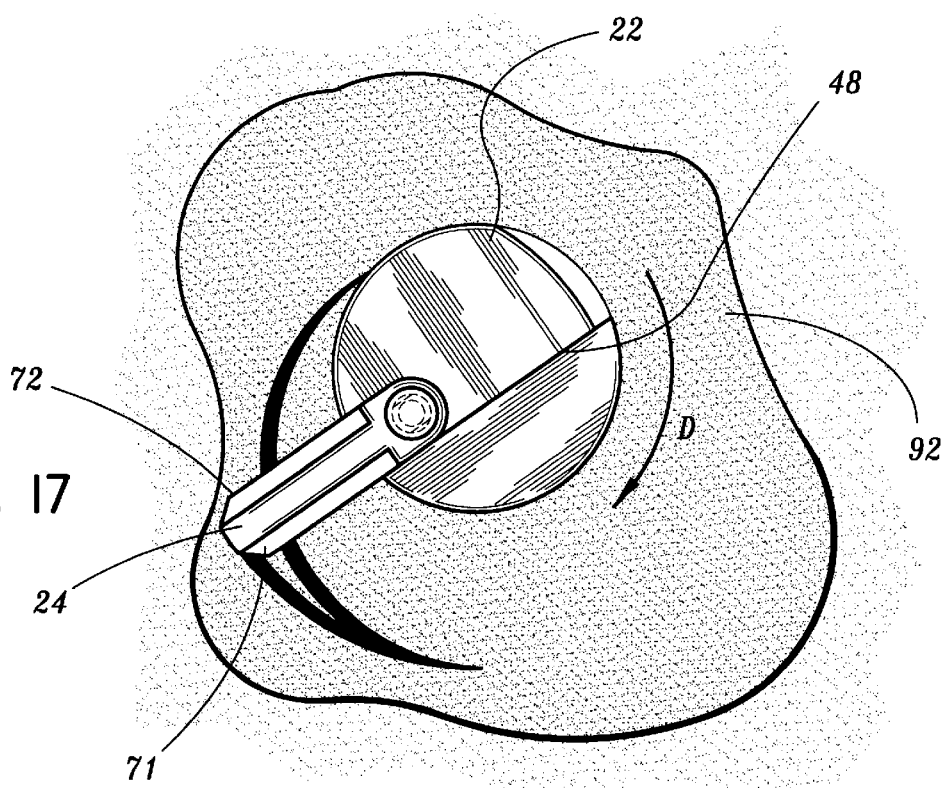
FIG. 17 is a side view of a distal end portion of a rod having the blade in a deployed position and beginning to rotate to cut tissue.

Referring to FIGS. 16 and 17, blade 24 is rotated into the deployed position by cutting through tissue with side cutting edge 71. Blade 24 is rotated to abut step 48. Cutting edge 72 is disposed opposite step 48 and is ready to begin cutting tissue. Rod 22 is rotated in the direction of arrow "D" by turning gear 44 (FIG. 7) such that the rotation causes cutting edge 72 to slice into target tissue mass 92. By abutting step 48, blade 24 is prevented from rotating in the direction opposite arrow "D" and blade 24 is able to apply a shearing force to cut tissue.

Figure 7:
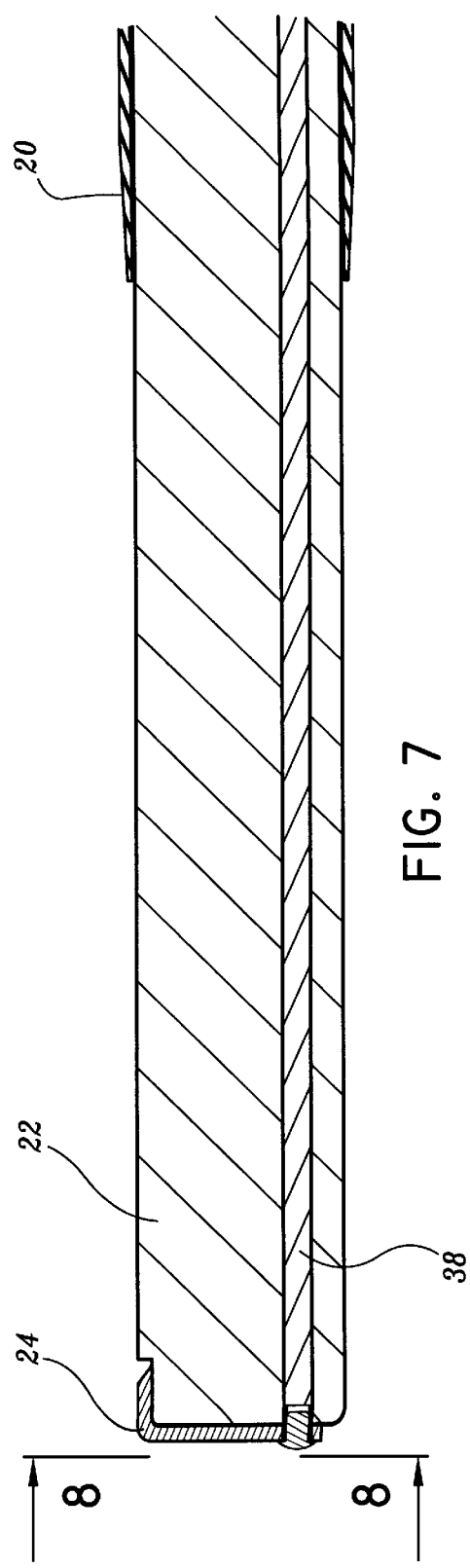
FIG. 7 is an enlarged view of the area of detail as shown in FIG. 6.
Figure 8:
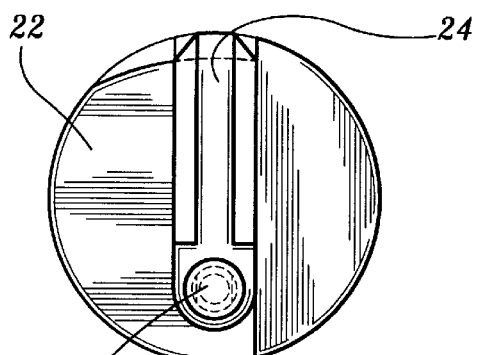
FIG. 8 is an end view taken at section line 8—8 as shown in FIG. 7.
Figure 9:
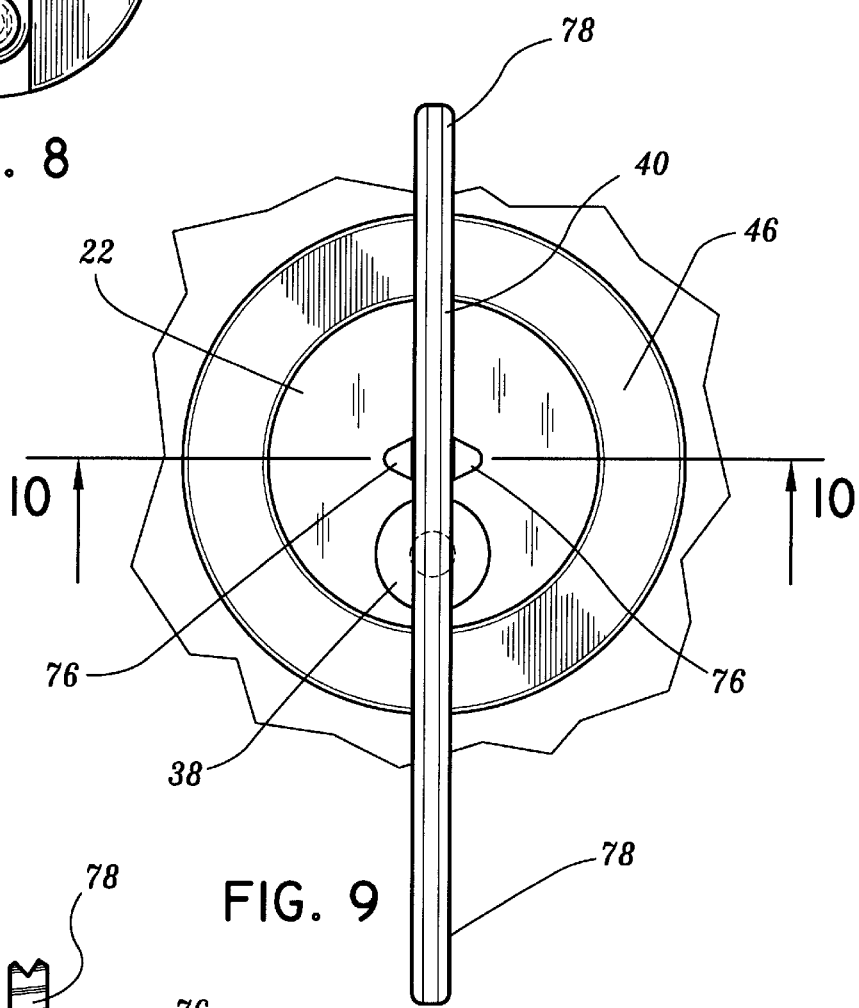
FIG. 9 is an end view taken at section line 9—9 as shown in FIG. 6.
Figure 10:
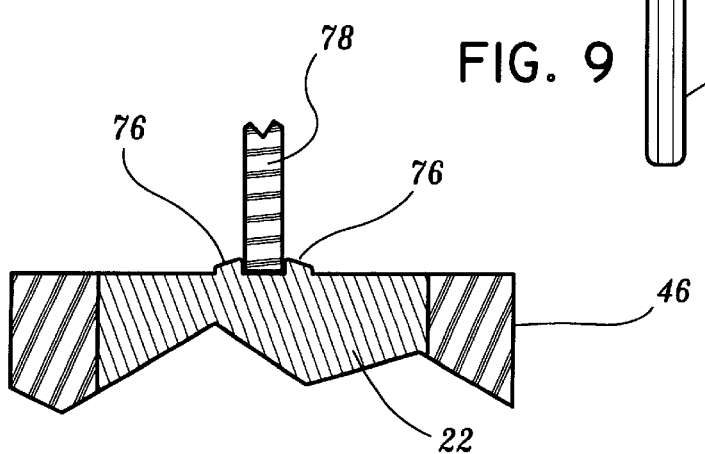
FIG. 10 is a cross-sectional view taken at section line 10—10 as shown in FIG. 9.
Figure 19:
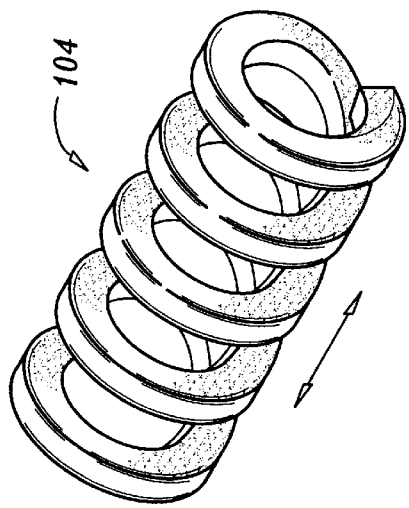
FIG. 19 is a perspective view of a tissue sample after being severed.
Figure 18:
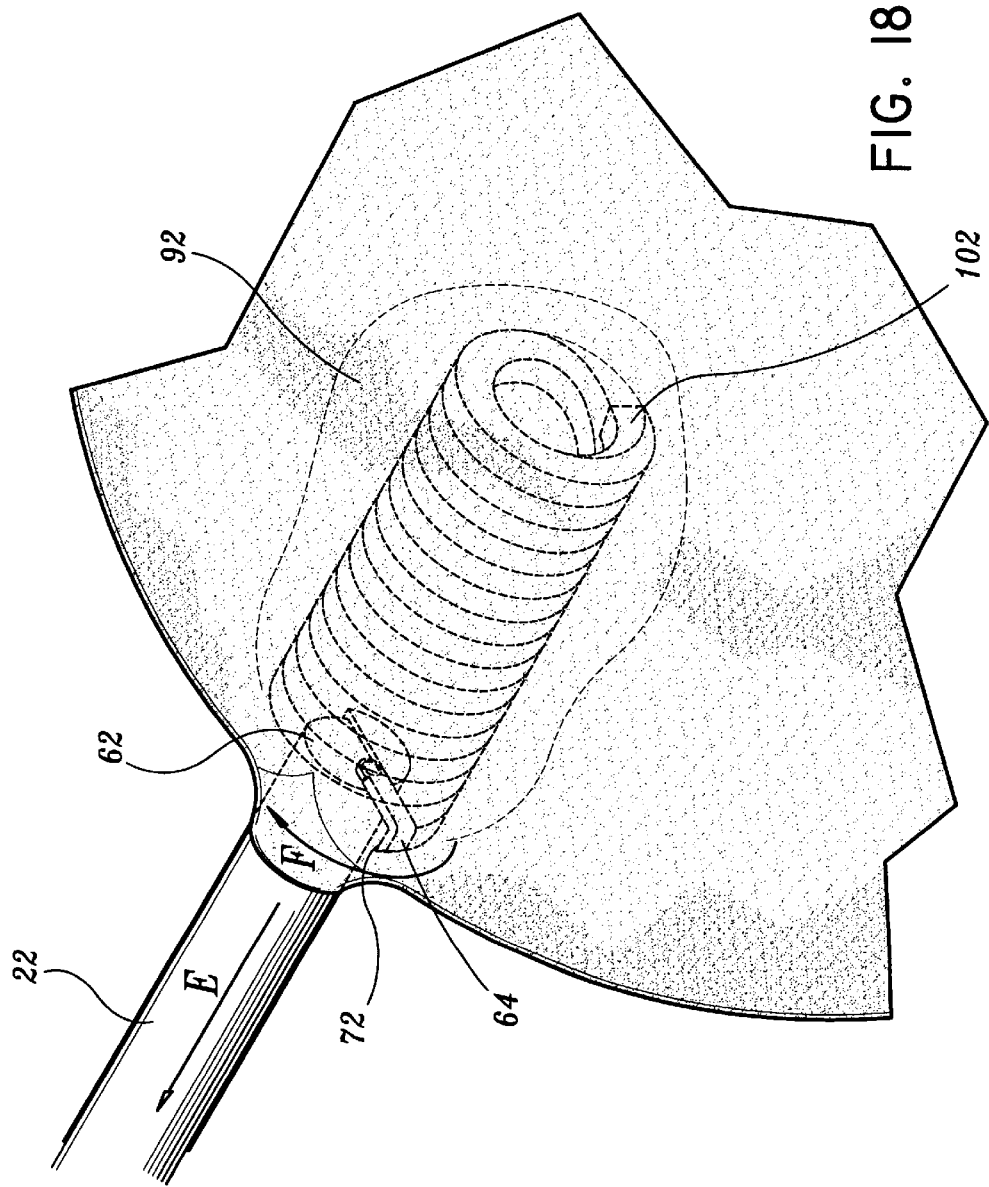
FIG. 18 is a perspective view showing a spiral cut made by rotating and proximally retracting the blade through a target tissue mass.

Referring to FIG. 18, the motion of rod 22 is controlled by gear 44 (FIG. 7). A spiral cut 102 is made in target tissue mass 92 by simultaneously rotating rod 22 in the direction of arrow "F" and translating rod 22 proximally (in the direction of arrow "E"). Preferably, the rate of rotation and the rate of translation are related to ensure that a continuous tissue sample 104 is achieved. For example, one rotation of blade 24 should correspond to a retraction of rod 22 equal to one angled leg portion 64 of blade 24 length. FIG. 19 shows tissue sample 104 stretched to show the shape of tissue sample 104 after being cut.

After the desired length of tissue has been cut, blade is rotated back to its stowed position thereby completing the cut to tissue sample 104 by slicing the end of tissue sample 104 between recess 62 of rod 22 and cutting edge 72 of blade. Tissue sample 104 is now completely severed from target tissue mass 92 (see FIG. 19). Slide 18 is detached and support tube 20 is left within breast 88. A vacuum tube can now be applied to support tube 20 to extract tissue sample 104. Alternately, the tissue sample may be manually extracted by, for example, forceps.

Referring now to FIGS. 20–23, an alternate embodiment of the biopsy apparatus is shown having a penetrating tip 200 attached to a distal end portion 202 of a rod 204. Rod 204 defines a transverse cut 206 therein. Rod 204 further defines a recess 208 for stowing an angled leg portion 210 of a blade 212. Rod 204 and blade 212 are structurally and functionally the same as described hereinabove. Penetration tip 200 obviates the need for a separate device or needle to form a hole in the breast prior to inserting rod 204. FIGS. 20 and 21 show blade 212 in a stowed position. FIGS. 22 and 23 show blade 212 in a deployed position.

It will be understood that various modifications may be made to the embodiments disclosed herein. For example, the key may be replaced by an automated mechanism which indexes the blade between the stowed and deployed positions. Therefore, the above description should not be construed as limiting, but merely as exemplifications of preferred embodiments. Those skilled in the art will envision other modifications within the scope and spirit of the claims appended hereto.

What is claimed is:

1. A biopsy apparatus for obtaining tissue samples comprising:
   a housing;
   an elongated member slidably and rotatably mounted in the housing; and
   a blade having a stem portion pivotally mounted on the elongated member, and the blade being movable transversely relative to a longitudinal axis of the elongated member and configurable between a stowed position and a deployed position wherein the blade is disposed a predetermined distance outwardly away from an outer surface of the housing to facilitate cutting of tissue situated outwardly away from the outer surface of the housing.

2. A biopsy apparatus as recited in claim 1 wherein the blade has an angled leg portion transversely orientated relative to the stem portion and substantially parallel to the longitudinal axis of the elongated member.

3. A biopsy apparatus as recited in claim 2 wherein the elongated member defines a recess for stowing the angled leg portion of the blade when in its stowed position.

4. A biopsy apparatus as recited in claim 1 further comprising an actuator operatively associated with the blade to move the blade between the stowed and deployed positions.

5. A biopsy apparatus as recited in claim 4 wherein the actuator includes a shaft rotatably disposed within the elongated member which rotates the blade.

6. A biopsy apparatus as recited in claim 5 wherein the shaft is turned by a key attached at a proximal end of the shaft.

7. A biopsy apparatus as recited in claim 6 wherein the key is selectively movable from a first position corresponding to the stowed position of the blade and a second position corresponding to the deployed position of the blade.

8. A biopsy apparatus as recited in claim 7 wherein the elongated member has stops formed thereon to secure the key in the first position corresponding to the stowed position of the blade and the second position corresponding to the deployed position of the blade.

9. A biopsy apparatus as recited in claim 1 wherein a distal end of the elongated member further includes a step thereon for preventing rotation of the blade during operation in the deployed position.

10. A biopsy apparatus as recited in claim 1 wherein the housing is adapted for mounting on a guidance system.

11. A biopsy apparatus as recited in claim 1 wherein a penetrating tip is mounted at a distal end of the elongated member.

12. A biopsy apparatus as recited in claim 1 wherein the blade is dimensioned and configured to be positioned a first distance away from a central longitudinal axis of the elongated member in the stowed position and a second distance away from the central longitudinal axis of the elongated member in the deployed position.

13. A biopsy apparatus as recited in claim 1 further comprising a gear shaft with a gear mounted thereon, the gear shaft attaching to the elongated member and positioned on the housing such that translation and rotation of the elongated member are controlled by translating and rotating the gear.

14. A biopsy apparatus for obtaining tissue samples comprising:
   a housing;
   an elongated member slidably and rotatably mounted in the housing; and
   a blade having a stem portion pivotally mounted on the elongated member and the blade being movable transversely to a longitudinal axis of the elongated member and configurable between a stowed position and a deployed position wherein the blade is disposed a predetermined distance outwardly away from an outer surface of the housing to facilitate cutting of tissue situated outwardly away from the outer surface of the housing; and
   a shaft rotatably disposed within the elongated member which attaches to and rotates the blade between the stowed position and the deployed position, the shaft being turned by an actuator attached at a proximal end of the shaft.

15. A biopsy apparatus as recited in claim 14 wherein the blade has an angled leg portion transversely orientated relative to the stem portion and substantially parallel to the longitudinal axis of the elongated member.

16. A biopsy apparatus as recited in claim 15 wherein the elongated member defines a recess for stowing the angled leg portion of the blade when in its stowed position.

17. A biopsy apparatus as recited in claim 14 wherein the elongated member has stops formed on a proximal end for securing the actuator in a first position corresponding to the stowed position of the blade and a second position corresponding to the deployed position of the blade.

18. A biopsy apparatus as recited in claim 14 wherein a distal end of the elongated member further includes a step thereon for preventing rotation of the blade during operation in the deployed position.

19. A biopsy apparatus as recited in claim 14 wherein the housing is adapted for mounting on a guidance system.

20. A biopsy apparatus as recited in claim 14 wherein a penetrating tip is mounted at a distal end of the elongated member.

21. A biopsy apparatus as recited in claim 14 wherein the elongated member defines a recess for stowing the angled leg portion of the blade when in its stowed position.

22. A biopsy apparatus as recited in claim 14 which further comprises a gear shaft with a gear mounted thereon, the gear shaft attaching to the elongated member and positioned on the housing such that translation and rotation of the elongated member are controlled by translating and rotating the gear.

23. A biopsy apparatus as recited in claim 14 wherein the blade is dimensioned and configured to be positioned a first distance away from a central longitudinal axis of the elongated member in the stowed position and a second distance away from the central longitudinal axis of the elongated member in the deployed position.

24. A biopsy apparatus for obtaining tissue samples comprising:

a housing;

an elongated member slidably and rotatably mounted in the housing;

a blade having a stem portion pivotally mounted on the elongated member and the blade being movable transversely relative to a longitudinal axis of the elongated member between a stowed position and a deployed position wherein the blade is disposed a predetermined distance outwardly away from an outer surface of the housing to facilitate cutting of tissue situated outwardly away from the outer surface of the housing the blade having an angled leg portion transversely orientated relative to the stem portion and substantially parallel to the longitudinal axis;

a shaft rotatably disposed within the elongated member which attaches to and rotates the blade between the stowed position and the deployed position, the shaft being turned by a actuator attached at a proximal end of the shaft; and the elongated member having stops formed on a proximal end for securing the actuator in a first position corresponding to the stowed position of the blade and a second position corresponding to the deployed position of the blade and a distal end of the elongated member having a step thereon for preventing rotation of the blade during operation in the deployed position, the elongated member defining a recess for stowing the angled leg portion of the blade when in its stowed position.

25. A biopsy apparatus as recited in claim 24 wherein the housing is adapted for mounting on a guidance system.

26. A biopsy apparatus as recited in claim 24 wherein a penetrating tip is mounted at a distal end of the elongated member.

27. A biopsy apparatus as recited in claim 24 which further comprises a gear shaft with a gear mounted thereon, the gear shaft attaching to the elongated member and positioned on the housing such that translation and rotation of the elongated member are controlled by translating and rotating the gear.

28. A biopsy apparatus as recited in claim 24 wherein the blade is dimensioned and configured to be positioned a first distance away from a central longitudinal axis of the elongated member in the stowed position and a second distance away from the central longitudinal axis of the elongated member in the deployed position.

29. A method of sampling tissue comprising the steps of:

providing a housing, an elongated member slidably and rotatably mounted in the housing and a blade having a stem portion pivotally mounted on the elongated member, and the blade being movable transversely to a longitudinal axis of the elongated member and configurable between a stowed position and a deployed position;

inserting the elongated member into a tissue mass;

deploying the blade;

severing a tissue sample from the tissue mass by proximally retracting and rotating the elongated member;

removing the elongated member from the tissue mass; and extracting the tissue sample from a patient.

30. The method of sampling tissue as recited in claim 29 wherein the step of inserting the elongated member comprises:

clamping a breast;

incising the breast at a predetermined location; and distally advancing the elongated member being guided by a guidance system through the incision and into the tissue mass.

31. The method of sampling tissue as recited in claim 29 wherein the step of deploying comprises:

rotating a shaft disposed within the elongated member and attached to the blade at a distal end of the shaft to rotate the blade from a stowed position to a deployed position; and securing the blade in the deployed position.

32. The method of sampling tissue as recited in claim 29 wherein the blade has an angled leg portion transversely orientated relative to the stem portion and substantially parallel to the longitudinal axis of the elongated member wherein the step of severing comprises:

rotating the elongated member; and proximally retracting the elongated member at a rate of the longitudinal distance of one angled leg portion of the blade per rotation to create a spiral cut to sever a tissue sample from the tissue mass.

* * * * *